United States Patent [19]

Nollet et al.

[11] Patent Number: 4,686,061

[45] Date of Patent: Aug. 11, 1987

[54] P-SULPHOPHENYL CARBONATES AND DETERGENT COMPOSITIONS AND DETERGENT ADDITIVES CONTAINING THESE COMPOUNDS

[75] Inventors: Andreas J. H. Nollet, Hilversum; John Meijer, Deventer; Johannes W. A. Overkamp, Raalte, all of Netherlands

[73] Assignee: Akzo NV, Arnhem, Netherlands

[21] Appl. No.: 881,960

[22] Filed: Jul. 3, 1986

[30] Foreign Application Priority Data

Jul. 3, 1985 [NL] Netherlands .......................... 8501902

[51] Int. Cl.$^4$ .......................... C07C 69/96; C11D 3/34; C11D 3/395; D06L 3/02
[52] U.S. Cl. ...................................... 252/95; 252/89.1; 252/99; 252/182; 252/186.38; 252/539; 252/558; 558/268; 558/271
[58] Field of Search .................. 252/89.1, 95, 99, 182, 252/186.38, 539, 558; 558/268, 271

[56] References Cited

U.S. PATENT DOCUMENTS

| | | | |
|---|---|---|---|
| 2,443,741 | 6/1948 | Kropa | 558/276 |
| 3,256,198 | 6/1966 | Matzner | 252/99 |
| 3,272,750 | 9/1966 | Chase | 252/99 |
| 3,549,682 | 12/1970 | Vernaleken | 558/271 |
| 3,686,127 | 8/1972 | Boldingh | 252/99 |
| 3,716,572 | 2/1973 | Moore | 558/268 |
| 4,444,674 | 4/1984 | Gray | 252/95 |
| 4,539,130 | 9/1985 | Thompson | 252/94 |

*Primary Examiner*—Dennis L. Albrecht
*Attorney, Agent, or Firm*—Parkhurst & Oliff

[57] ABSTRACT

This disclosure relates to novel compounds of the class of the p-sulphophenyl carbonates, viz. mono-p-sulphophenyl carbonates derived from ethoxylated alcohols and bis-p-sulphophenyl dicarbonates derived from alkane diols and poly(ethylene glycols). The novel compounds are efficient bleaching activators. The disclosure also relates to detergent additives and detergent compositions wherein the novel compounds are contained.

4 Claims, No Drawings

P-SULPHOPHENYL CARBONATES AND DETERGENT COMPOSITIONS AND DETERGENT ADDITIVES CONTAINING THESE COMPOUNDS

The invention relates to a compound of the general structural formula:

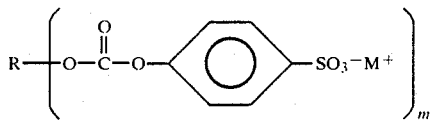

where R represents an organic group, $M^+$ a cation, and m a natural number. The invention also relates to a detergent composition and a detergent additive in which this compound is used as bleaching activator.

A compound of the type indicated above and similar compositions are disclosed in U.S. Pat. No. 3,272,750. It describes the use of such a compound, where m has the value of 1, as bleaching activator in combination with conventional bleaching agents, such as percarbonate and perborate in order to obtain sufficient bleaching action in the removal of stains from textile materials at a temperature of 60° C. or lower, as usually applied in modern washing machines; at such a temperature the conventional bleaching agents are not or insufficiently active without the use of activators.

Said patent specification describes bleaching activators of the general formula $R_1O.CO.OR_2$, where $R_1$ represents an electron attracting group and $R_2$ is a substituted or unsubstituted alkyl group, aryl group or alicyclic group; as electron attracting groups are mentioned the p-sulphophenyl group and the p-carboxyphenyl group. As p-sulphophenyl carbonates said patent specification specifically mentions compounds where $R_2$ is a methyl, ethyl, n-propyl, n-butyl, phenyl or benzyl group and the sodium ion is used as counterion. These prior art compounds, however, have not found any commercial application.

The invention has for its object to provide novel compounds of the class of the p-sulphophenyl carbonates which as compared with the p-sulphophenyl carbonates known from the above-mentioned patent specification are just about as effective or even more effective. Moreover, their bleach activating action is superior to that of tetraacetylethylenediamine (TAED), which at present is the most widely used commercial bleaching activator.

The compound according to the invention is characterized in that m has a value not higher than 2, where, when m=1, R corresponds to the general formula:

where R' represents an alkyl group containing 1-8 carbon atoms and n has a value of 2-3, and when m=2, R represents an alkylene group containing 2-14 carbon atoms or corresponds to the general formula

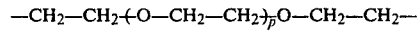

where p has a value of 0-10.

The earlier, non-prepublished European Patent Application No. 0 166 571 describes a great many bleaching activators of the general formula $[RX]_m$ AL wherein
m has a value of 1 to 2
X may represent 0
A may represent

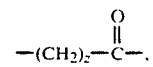

with z being an integer from 0 to 2
L may represent a p-oxybenzenesulphonate
R may represent an ethoxylated $C_1$-$C_{20}$ hydrocarbyl group with one or more EO units, especially $C_{10}$-$C_{18}$ alkyl with above about 3 EO units, especially 5-15 EO units.

Said patent application, however, does not disclose any of the compounds of the present invention.

The present compounds may be divided into mono-p-sulphophenyl carbonates (m=1) and bis-p-sulphophenyl dicarbonates (m=2) (see general structural formula 1).

In the case of the mono-p-sulphophenyl carbonates R in the general structural formula is to correspond to

where R' is an alkyl group containing 1-8 carbon atoms and n has a value of 2-3. The alkyl group may be linear or branched. As examples thereof may be mentioned methyl, ethyl, n-butyl, 2-ethylhexyl and n-octyl. In the case of the bis-p-sulphophenyl dicarbonates R in the general structural formula is an alkylene group containing 2-14 carbon atoms or a group of the general formula

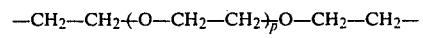

where p has a value in the range of 0-10. The alkylene group may be linear or branched. Examples thereof include ethylene, propylene, trimethylene, tetramethylene, hexamethylene, octamethylene and decamethylene. Examples of suitable cations $M_+$ are alkali metal ions and the ammonium ion. Preferably, $M^+$ represents a sodium ion or a potassium ion.

Of the compounds according to the invention the bis-p-sulphophenyl dicarbonates are preferred.

The present compounds may be prepared in a known manner by converting an alcohol or a diol with phosgene into a chloroformate or bis-chloroformate which is subsequently reacted with 4-hydroxybenzenesulphonic acid in the presence of, say, sodium hydroxide to form the p-sulphophenyl carbonate desired.

As examples of alcohols which may be used in the preparation of the present mono-p-sulphophenyl carbonates may be mentioned diethylene glycol monomethyl ether, ethoxylated (2EO) n-butanol, ethoxylated (3EO) n-butanol, ethoxylated (3EO) 2-ethyl hexanol and ethoxylated (3EO) n-octanol. As examples of diols that may be used in the preparation of the present bis-p-sulphophenyl dicarbonates may be mentioned 1,2-ethanediol (glycol), 1,2-propanediol (propylene glycol), 1,3-propanediol, 1,4-butanediol, 1,5-pentanediol 1,6-hexanediol, 1,8-octanediol, 1,10-decanediol, 1,12-dodecanediol, diethylene glycol, triethylene glycol, tetraethylene glycol and poly(ethylene glycols) having molecular weights of 200, 300 and 400.

As mentioned above, the compound according to the invention is an effective bleach activator. The compound is therefore advantageously incorporated into a solid detergent composition which, in addition to the bleach activator, contains a bleaching agent, which under alkaline conditions generates hydrogen peroxide, and a surfactant. Also mixtures of the present compounds may be used to that end.

The amount of bleaching activator in the present detergent composition is preferably so chosen that the molar ratio to the activator of the hydrogen peroxide latent in the bleaching agent is in the range of 1:1 to 20:1.

Examples of suitable, commonly used bleaching agents include alkali metal percarbonates, perborate, persilicate and perpyrophosphate.

Suitable surfactants for use in the present composition are the anionic, non-ionic and amphoteric surface active agents generally employed for this purpose. As examples thereof may be mentioned soaps of synthetic and natural fatty acids, alkyl benzene sulphonates, aliphatic sulphonates, fatty alcohol sulphates, sulphates of alkoxylated fatty alcohols, addition products of ethylene oxide to fatty alcohols, ethylene oxide/propylene oxide copolymers and carboxyl group-, sulphate group- or sulphonate group-containing betaines.

In addition to a bleaching agent, a bleaching activator and a surfactant the present composition may contain the additives usually employed for solid detergent compositions, such as sequestering agents, fillers, builders, enzymes, fluorescent and optical brightening or whitening agents, dirt suspending agents and foam suppressors.

In actual practice the detergent composition according to the invention may be in a form varying from powdered to granular and may be prepared by methods known in the art, such as crystallization or spray drying of an aqueous slurry or mechanical mixing of the substances. The bleaching activator according to the invention may be applied as such, or while provided on a carrier material. Examples of suitable carrier materials are sodium chloride, potassium chloride and sodium sulphate. Coated particles are also contemplated (see below).

The present bleaching activator may also be added separately, in the form of a detergent additive containing the bleaching activator and a carrier material, to aqueous wash liquor containing at least a surfactant and a hydrogen peroxide generating bleaching agent. To this end the bleaching activator may preferably be applied in the form of powder provided on a solid carrier, such as sodium chloride, potassium chloride or sodium sulphate, or in the form of a solution or dispersion. The bleaching activator may also be used in the form of coated particles; examples of suitable coating materials are (ethoxylated) fatty acids and poly(ethylene oxide). Alternatively, the bleaching activator may have been introduced into a sachet or combined with a flexible substrate, as described for acyl group-containing bleaching activators in European Patent Specification No. A1-120591. Such a detergent additive may also contain mixtures of the present bleaching activators and other active washing agents. As far as the latter agents are concerned the choice of them is of course dependent on the compatibility with the present activator. This is of special importance when the additive is used in the form of a solution or dispersion.

The following examples serve to illustrate the invention. All percentages in them are by weight.

EXAMPLE 1

In this Example a description is given of a general procedure used for preparing the present compounds. The scheme below gives the reaction conditions and the reaction results for seven compounds.

To a stirred solution in 100 g of water of 0.1 mole of sodium 4-hydroxybenzene sulphonate dihydrate and 0.1 mole of sodium hydroxide there was added dropwise over a period of 5–10 minutes 0.11 moles of chloroformate (in the case of Compounds 1 and 2) or 0.055 moles of bischloroformate (in the case of Compounds 3–7) at a temperature not higher than 30° C. Stirring was continued at a temperature between 20° and 30° C. until a clear reaction mixture was obtained. Subsequently, volatiles (including water) were removed by evaporation in vacuo (1.5 mbar, 30° C.). The solid mass obtained was finally dried at 35° C. until its weight remained constant.

All products were isolated as white powders and their structure was confirmed by IR and NMR analyses. NMR analysis was also applied to determine the contents of the active compounds using p-toluenesulphonic acid as the reference compound. The yields were calculated on the amount of sodium 4-hydroxybenzene sulphonate.

Scheme

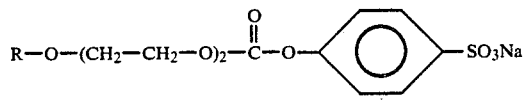

| Compound No. | R | reaction time (min) | content (%) | yield (%) |
|---|---|---|---|---|
| 1 | $CH_3$ | 5 | 81,2 | 94,5 |
| 2 | $n\text{-}C_4H_9$ | 5 | 84,9 | 99,3 |

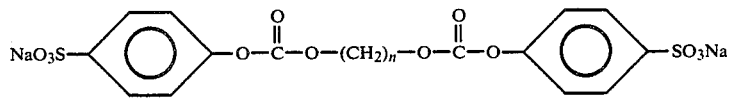

| Compound No. | n | reaction time (min) | content (%) | yield (%) |
|---|---|---|---|---|
| 3 | 2 | 10 | 71,5 | 84,8 |
| 4 | 4 | 45 | 78,6 | 96,6 |
| 5 | 6 | 60 | 81,0 | 99,7 |

-continued
Scheme

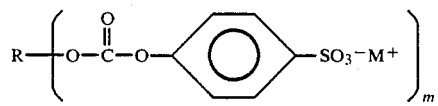

| Compound No. | p | reaction time (min) | content (%) | yield (%) |
| --- | --- | --- | --- | --- |
| 6 | 2 | 15 | 77.1 | 95.9 |
| 7 | 4 | 40 | 79.2 | 95.1 |

EXAMPLE 2

The Compounds 1–7 described in Example 1 were tested for their bleach activating action as follows.

Imidial Grün pieces of test cloth (from the laundry research institute Krefeld, W-Germany) of 5×5 cm were treated for 30 minutes at 40° C. and 60° C. with 150 ml of an aqueous (5° GH) solution containing per liter 5.16 g of a standard detergent, 0.69 g of sodium perborate and 2.5 or 1.25 mmoles (see below) of bleaching activator. The standard detergent was of the following composition;

8% sodium linear alkyl (average $C_{11\frac{1}{2}}$) benzene sulphonate;
2.9% ethoxylated (14 EO) talc alcohol;
3.5% sodium soap (13–26% $C_{12-16}$; 74–78% $C_{18-22}$)
43.7% sodium triphosphate;
7.5% sodium silicate ($SiO_2$:$Na_2O$=3.3:1);
1.9% magnesium silicate;
1.2% carboxymethyl cellulose;
0.3% sodium ethylene diamine tetraacetate;
0.3% optical whitening agent for cotton (stilbene type);
21% sodium sulphate;
9.7% water.

Subsequently, the pieces of cloth were rinsed in tap water and dried to the air. The amount of colouring agent left on each piece of cloth was determined with the aid of a reflectometer by measuring the light reflected in all directions at an angle of 45° of a beam of tristimulus blue light directed perpendicular to the piece of cloth. The value found was compared with that determined on a piece of cloth washed under similar conditions but without a bleaching activator present in the wash solution and the diffrence expressed in the value $\Delta R$; the higher this value, the better the bleaching action and, hence, the effectiveness of the activator.

The amounts of bleaching activator used were 2.5 mmoles per liter of Compounds 1 and 2 and 1.25 mmoles per liter of Compounds 3–7. The values of $\Delta R$ found are given in the Table.

TABLE

| Compound | $\Delta R$ (40° C.) | $\Delta R$ (60° C.) |
| --- | --- | --- |
| 1 | 3,5 | 4,6 |
| 2 | 6,5 | 7,6 |
| 3 | 1,4 | 2,5 |
| 4 | 2,8 | 3,8 |
| 5 | 4,7 | 5,5 |
| 6 | 1,8 | 2,6 |
| 7 | 3,0 | 3,0 |

In comparative experiments carried out using 2.5 mmoles per liter of sodium p-sulphophenyl ethyl carbonate and sodium p-sulphophenyl n-butyl carbonate, which are both bleaching activators according to U.S. Pat. No. 3,272,750, values of $\Delta R$ ranging from 0.5 to 6.9 at 40° C. and from 1.5 to 7.9 at 60° C. were found. In another comparative experiment carried out using 1.25 mmoles per liter of tetraacetylethylenediamine (TAED) the $\Delta R$ values found were 0 at 40° C. and 1.5 at 60° C.

From this Example it follows that the bleaching activators according to the invention are about as or more effective than prior art p-sulphophenyl alkyl carbonates and that they are superior to TAED.

We claim:

1. A compound of the general structural formula:

where R represents an organic group, $M^+$ a cation and m a natural number, characterized in that m has a value not higher than 2, where when m=1, R corresponds to the general formula:

$$R'+O-CH_2-CH_2)_{\overline{n}}$$

where R' represents an alkyl group containing 1–8 carbon atoms and n has a value of 2–3, and when m=2, R represents an alkylene group containing 2–14 carbon atoms or corresponds to the general formula:

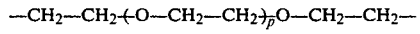

where p has a value in the range of 0 to 10.

2. A detergent additive comprising a bleaching activator and a carrier material, characterized in that the bleaching activator is a compound according to claim 1.

3. A detergent additive according to claim 2, characterized in that the carrier material is sodium chloride, sodium sulphate or a mixture thereof.

4. A solid detergent composition containing a surfactant, a bleaching activator, and a bleaching agent which generates hydrogen peroxide under alkaline conditions, characterized in that the bleaching activator is a compound according to claim 1.

* * * * *

UNITED STATES PATENT AND TRADEMARK OFFICE
CERTIFICATE OF CORRECTION

PATENT NO. : 4,686,061

DATED : August 11, 1987

INVENTOR(S) : Andreas J. H. NOLLET et al

It is certified that error appears in the above-identified patent and that said Letters Patent is hereby corrected as shown below:

Column 2, line 3, change "to" to --or--;

line 64, change "1,5-pentanediol" to --1,5-pentanediol,--.

Column 3, line 28, change "surfactant" to --surfactant,--.

Columns 3-6, Example 1, in the Scheme, change all commas to periods.

Column 5, line 53, change "differnce" to --difference--.

Columns 5-6, Example 2, in the Table, change all commas to periods.

Signed and Sealed this

Nineteenth Day of January, 1988

Attest:

DONALD J. QUIGG

Attesting Officer

Commissioner of Patents and Trademarks